United States Patent [19]
Takamoto et al.

[11] Patent Number: 5,894,345
[45] Date of Patent: *Apr. 13, 1999

[54] OPTICAL METHOD OF DETECTING DEFECT AND APPARATUS USED THEREIN

[75] Inventors: Kenji Takamoto, Suita; Kanji Nishii, Osaka; Masami Ito, Moriguchi; Atsushi Fukui, Osaka; Kazumasa Takata, Moriguchi, all of Japan

[73] Assignee: Matsushita Electric Industrial Co., Ltd., Japan

[ * ] Notice: This patent is subject to a terminal disclaimer.

[21] Appl. No.: 08/859,423

[22] Filed: May 20, 1997

[30] Foreign Application Priority Data

May 22, 1996 [JP] Japan ................. 8-126613

[51] Int. Cl.$^6$ ........................................ G01N 21/00
[52] U.S. Cl. ........................... 356/237.1; 356/239.1
[58] Field of Search ........................ 356/237, 239, 356/237.1, 239.1

[56] References Cited

U.S. PATENT DOCUMENTS

| | | |
|---|---|---|
| 4,555,179 | 11/1985 | Langerhole et al. ............ 356/237 |
| 5,137,355 | 8/1992 | Barbour et al. ............ 356/237 |
| 5,293,538 | 3/1994 | Iwata et al. ............ 356/237 |
| 5,699,153 | 12/1997 | Takamoto et al. ............ 356/237 |

FOREIGN PATENT DOCUMENTS

| | | |
|---|---|---|
| 64-54338 | 3/1989 | Japan. |
| 1-180436 | 7/1989 | Japan. |
| 4-174348 | 6/1992 | Japan. |
| 5-187831 | 7/1993 | Japan. |

*Primary Examiner*—Richard A. Rosenberger
*Attorney, Agent, or Firm*—Parkhurst & Wendel

[57] ABSTRACT

An array light source 1 with semiconductor laser sources disposed one-dimensionally and a projective lens 2 are used to illuminate an inspected object so that light beams projected from the array light source form a dotted line on the object. A line sensor is used to receive through an objective lens 3 light emitted from an imaging area 11 away from an illuminated area 12. An image signal, fed to an image processing unit 8 through a pre-processing unit 7 producing an image from signals from the line sensor 4 and a stage 5 is processed, while the stage 5 bearing the object 6 is being gradually moved, to inspect the object 6 for crack defects 9 and 10 by detecting an optically nonhomogeneous portion of the object. The method allows a crack defect of an object, such as a ceramic substrate or a sintered metal product, to be detected fast with high accuracy.

7 Claims, 19 Drawing Sheets

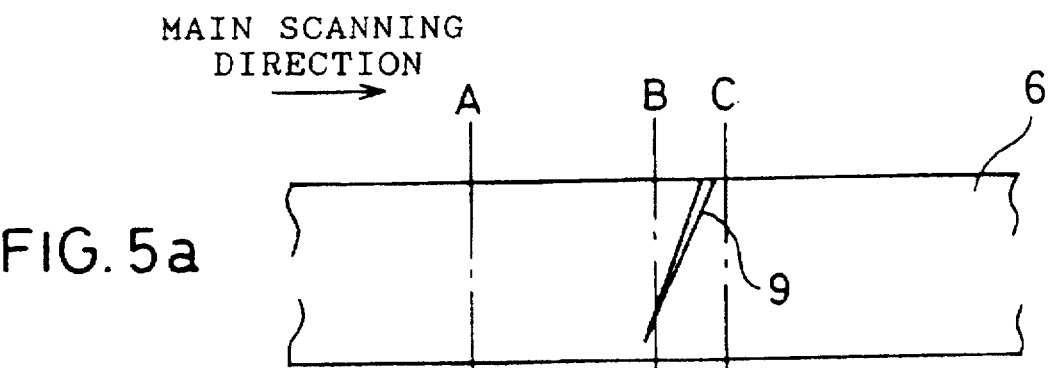
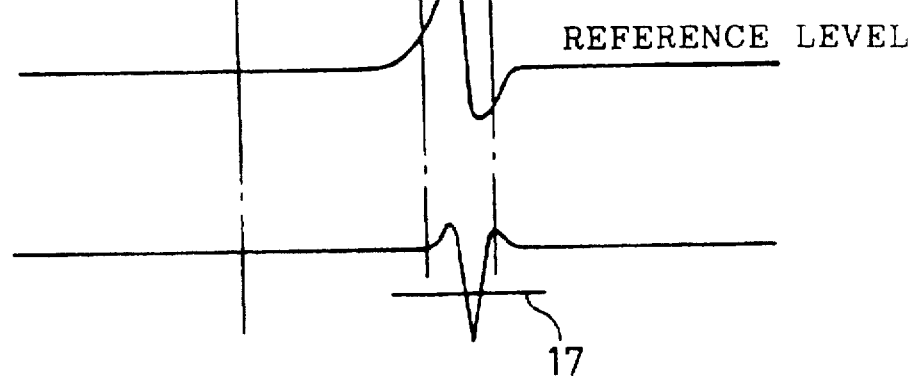
FIG. 5a
MAIN SCANNING DIRECTION
FIG. 5b
REFERENCE LEVEL
FIG. 5c

AUXILIARY SCANNING DIRECTION

MAIN SCANNING DIRECTION

FIG.13a MAIN SCANNING DIRECTION
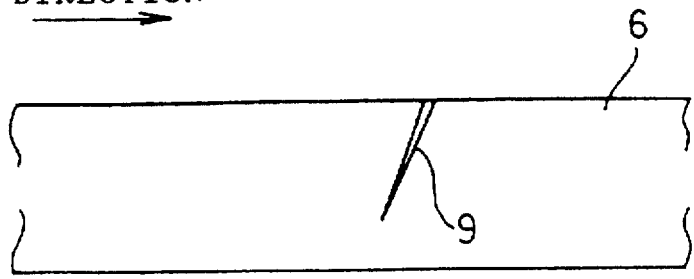
FIG.13b
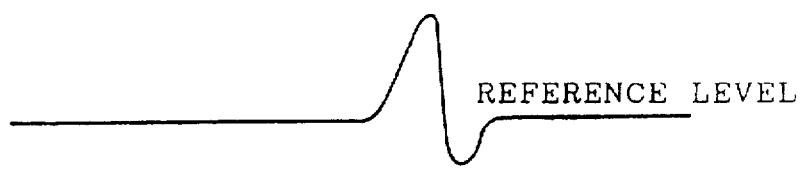
REFERENCE LEVEL
FIG.13c
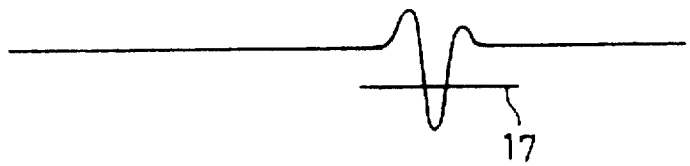
FIG.13d
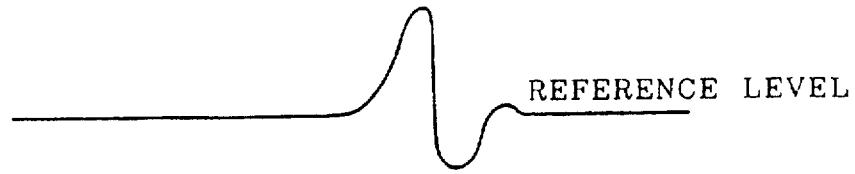
REFERENCE LEVEL
FIG.13e
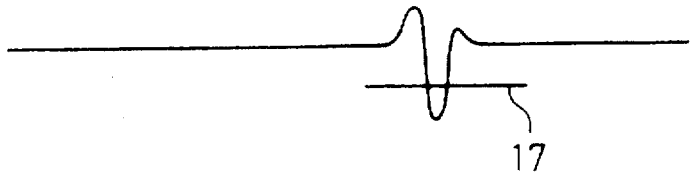

FIG.19a
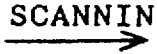
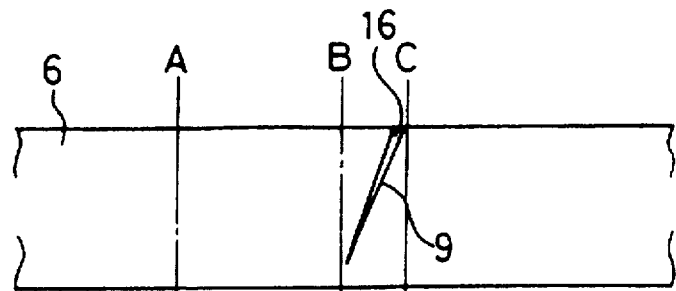
FIG.19b
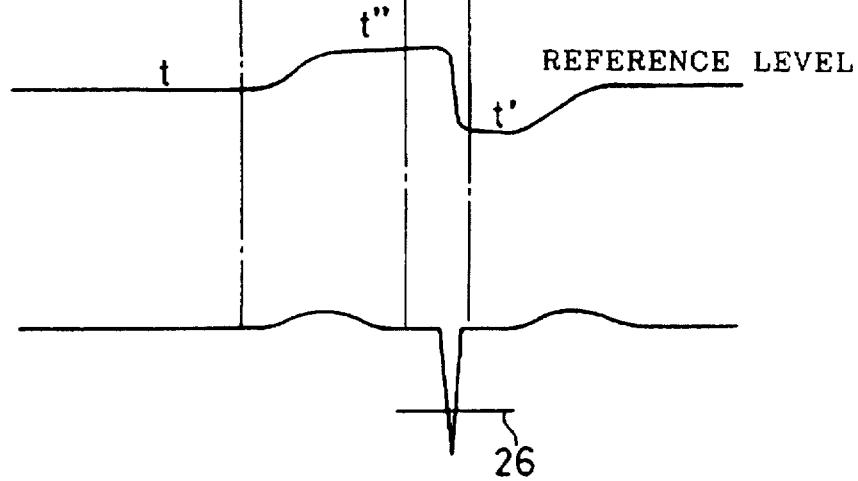
FIG.19c

AUXILIARY SCANNING
DIRECTION →

OPTICAL METHOD OF DETECTING DEFECT AND APPARATUS USED THEREIN

FIELD OF THE INVENTION

The present invention relates to an optical method of detecting an optically nonuniform portion or a nonuniform portion in terms of heat conduction at the surface of, or inside, an inspected object and to an apparatus used in the method.

BACKGROUND OF THE INVENTION

By way of example, defects in a ceramic substrate are described below. Various types of ceramics, including insulation ceramics and piezoelectric ceramics, are used for many machine parts as well as for electronic parts.

Cracks in a ceramic substrate diffusing light or air bubbles confined in the substrate cause its optical reflectance or transmittance locally to vary, thus making the substrate optically nonuniform. Similarly, cracks in a ceramic substrate diffusing a little light or air bubbles confined in the substrate cause its thermal conductivity locally to vary, and thus its temperature distribution becomes uneven. Minute defects at the surface of, or inside, ceramic substrates, including microcracks with an opening width on the order of submicrons, serve as start points of crack propagation, so that brittle fracture occurs. This behavior of such minute defects is a serious problem. Defects, especially crack defects at, or near, the surface of a substrate are considered to matter. The practical limit length of these crack defects is said to be 30 to 100 μm.

Known methods of detecting the defects above include visual inspection using an optical microscope or the like, liquid penetrant testing, ultrasonic testing, ultrasonic microscopy, radiological testing, and infrared thermography.

Visual inspection using an optical microscope or the like, however, has a problem of low accuracy of defect detection both because the size of defects to be detected, such as cracks, is small and because light microscopes bring out unclear contrast.

Defect detecting apparatuses are required to be inexpensive, since they are used in production lines to inspect inexpensive substrates. The apparatuses are also required to operate at high speed. Apparatuses accurately performing liquid penetrant testing, ultrasonic testing, ultrasonic microscopy, and radiological testing cannot meet either of the requirements above.

When an electrically conductive object is inspected by infrared, its heating distribution is measured when energized, or the temperature distribution over its face is imaged using a two-dimensional infrared sensor when its back is heated. However, if the object has high thermal conductivity, an uneven temperature distribution at a defect disappears immediately after the object is heated. This makes it difficult to detect a defect, where temperature distribution is uneven, thus posing a problem of low defect detection sensitivity.

DISCLOSURE OF THE INVENTION

In view of the foregoing, it is an object of the present invention to provide an optical method of detecting a defect by which a crack defect or the like in metal, ceramic substrates, and the like can accurately be detected fast no matter whether the metal and ceramic substrates diffuse light or not and to provide an apparatus used in the method.

To this end, according to the present invention, an optically nonuniform portion of an inspected object is detected by aiming light beams at the surface of the object so that their intensities differ from each other at the surface and measuring changes in the intensity of light emitted from the surface after the light beams enter the object.

The optical method enables a crack defect in an object to be detected fast with high accuracy.

BRIEF DESCRIPTION OF THE DRAWINGS

FIGS. 5a, 5b and 5c are schematic diagrams of a signal indicating that a crack defect in an auxiliary scanning direction has been detected in an arrangement of the first embodiment;

FIGS. 13a, 13b, 13c, 13d and 13e are schematic diagrams of a signal indicating that a crack defect in an auxiliary scanning direction has been detected in an arrangement of the fifth embodiment;

FIGS. 19a, 19b and 19c are schematic views of a signal indicating that a crack defect in an auxiliary scanning direction has been detected in an arrangement of the sixth embodiment.

DESCRIPTION OF THE EMBODIMENTS

Figure 1:
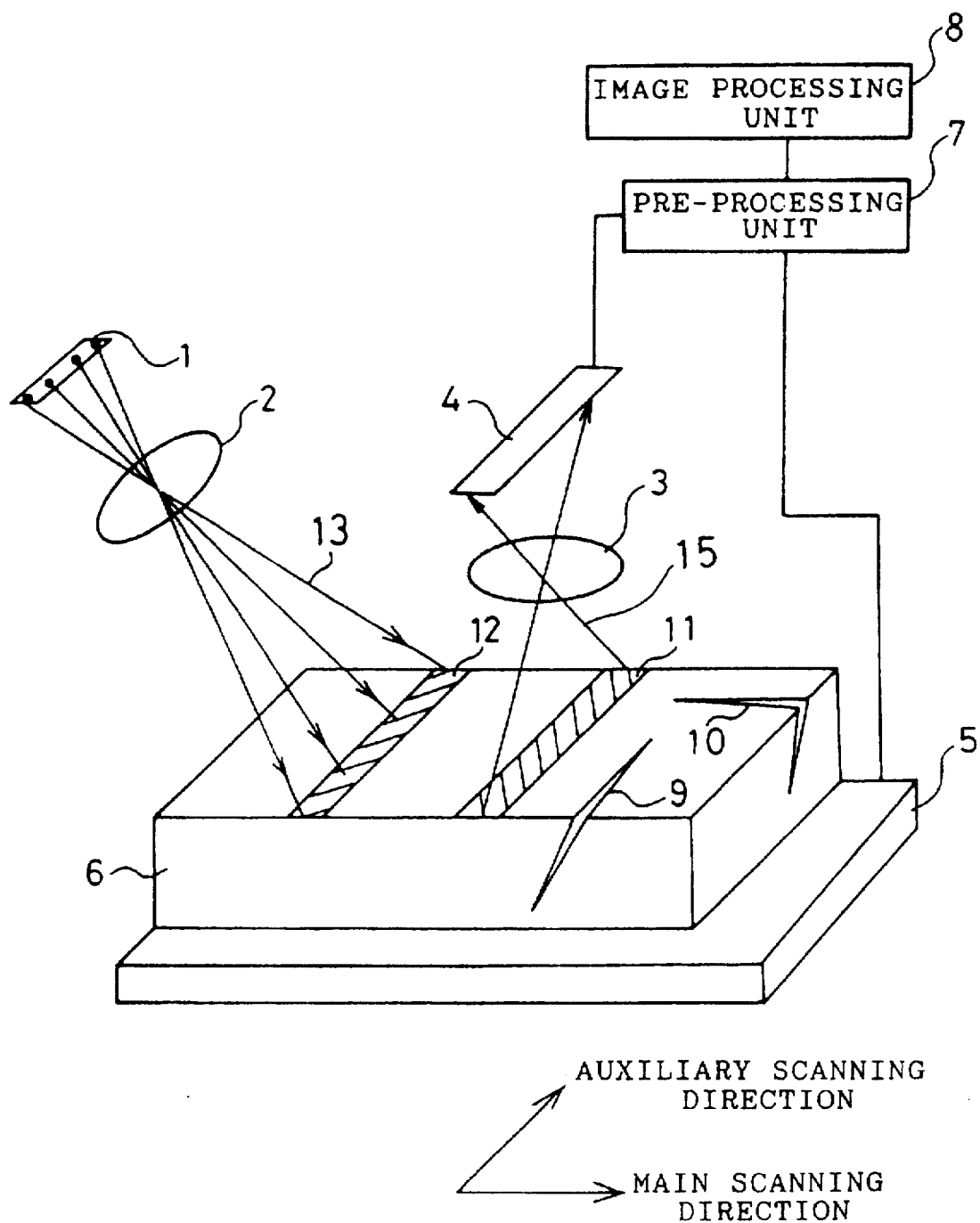
FIG. 1 is a block diagram of an apparatus using an optical method of detecting a defect, which apparatus carries out a first embodiment of the present invention.

Referring now to the drawings, the embodiments of the present invention are described below.

First Embodiment

FIG. 1 shows an arrangement of an optical defect detecting apparatus according to the first embodiment of the present invention.

The defect detecting apparatus according to the first embodiment has illuminating means, imaging means, drive means, and image processing means.

The illuminating means, consisting of an array light source 1 with semiconductor laser sources one-dimensionally disposed and a projecting lens 2, illuminates an inspected object 6 so that light beams, differing in intensity at the surface of the object, form a dotted line on the object.

The imaging means, consisting of an objective lens 3 and a line sensor 4 with CCD elements disposed in a line, detects light emitted from a linear imaging area 11 parallel to an illuminated area 12 formed on the object 6 by the illuminating means.

The drive means, consisting of a stage 5 moving the inspected object thereon in a predetermined direction, relatively moves the object 6 with respect to the illuminating means and imaging means.

The imaging processing means, consisting of a pre-processing unit 7 producing an image from a signal from a line sensor 4 and a movement signal from the stage 5 and of an image processing unit 8, detects an optically uneven portion of the object 6, using an imaging signal detected by the imaging means.

In the above arrangement, the projecting lens 2 projects light beams from the array light source 1 onto the object 6 to illuminate the object so that the light beams, differing in intensity at the surface of the object, form a dotted line on the object. The light beams 13 enter the object 6. Light beams 15 emitted from the surface of the object 6 contain information on the inside of the object 6. The light beams are called diffusion emission light herein. The diffusion emission light 15, diffused from the illuminated area 12 through the object 6 and emitted from the imaging area 11, is projected through the objective lens 3 of the imaging means on the line sensor 4.

While the object 6 is being moved using the stage 5, an image signal fed through the pre-processing unit 7 to the image processing unit 8 is processed to detect a crack defect in the object 6. Herein the direction in which the object 6 is moved is called the main scanning direction, and that in which scanning is performed using the line sensor 4 is called the auxiliary scanning direction. A detection procedure is described below, for example, for a crack defect 9 in the auxiliary scanning direction and a crack defect 10 in the main scanning direction, which defects are at right angles to each other.

In the first embodiment, the simplest way to detect the diffusion emission light 15 from the surface of the object 6, which contains information on the inside of the object 6, is by arranging the illuminated area 12, that is, a dotted line formed by light beams from the illuminating means 12 in parallel with the imaging area 11, with a separation interval between both areas, so that the two areas do not overlap. This arrangement prevents reflected light of high intensity from the illuminated area 12 from entering the line sensor 4 by accident, thus allowing only the diffusion emission light 15 of low intensity to be detected.

If an optically unhomogeneous portion, causing the reflectance and transmittance to change locally, is present in the object 6, the intensity of light emitted from part of the surface of the object, which part is near the portion, more significantly changes than that of light from other parts of the surface. The reason is described below.

Figure 2:
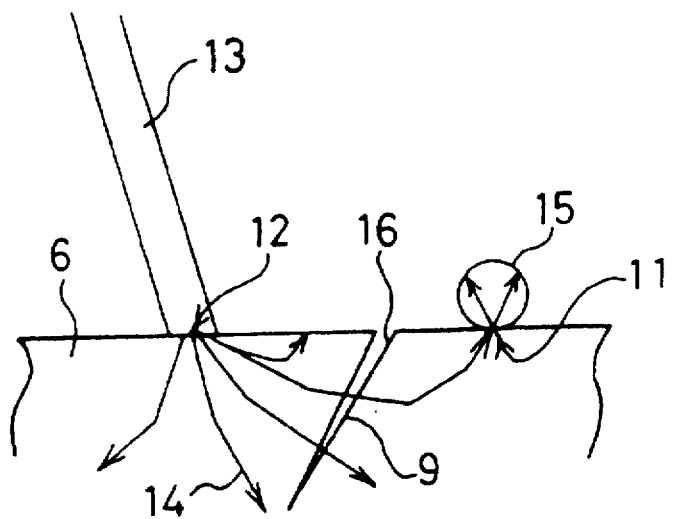
FIG. 2 is a schematic view illustrating how light diffuses when a crack defect is between an illuminated area and an imaging area in an arrangement of the first embodiment.
Figure 3:
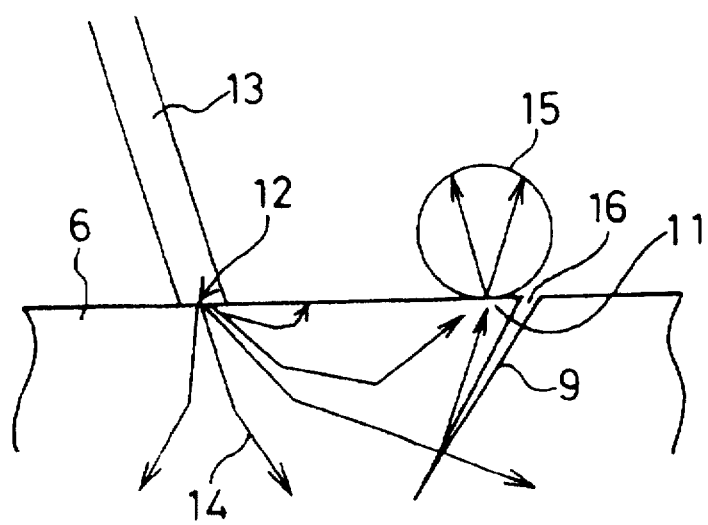
FIG. 3 is a schematic view illustrating how light diffuses when a crack defect is except between an illuminated area and an imaging area in an arrangement of the first embodiment.

FIGS. 2 and 3 are schematic cross-sectional views of a crack defect in the object 6, diffusing light.

When entering the object 6, some of the light beams 13 bend and then diffuse through the object 6, while attenuating exponentially. After reaching the imaging area 11, part of the diffused light 14 is emitted from the surface of the object 6. As shown in FIG. 2, the crack defect 9 has a cross section defined by crack surfaces facing each other in the object 6, having an index of refraction of n, and an air layer 16, having an index of refraction of 1, is in the crack defect. Since the index of refraction differs across the interface between the air layer 16 and the object, the optical reflectance and transmittance locally change, and thus the diffused light 14 in the object 6 is nonuniform.

As shown in FIG. 2, if the crack defect 9 is between the illuminated area 12 and the imaging area 11, part of the diffused light 14, diffused from the illuminated area 12 through the object 6, reaches the imaging area 11 through the crack defect 9. After passing through the crack defect 9 , diffused light further attenuates, so that the intensity of the diffusion emission light 15 from the imaging area 11 becomes lower, compared with a case where no crack defect is present.

As shown in FIG. 3, on the other hand, if the crack defect 9 is except between the illuminated area 12 and imaging area 11, and no crack defect is between the illuminated area 12 and imaging area 11, part of the diffused light 14 in the object is emitted as the diffusion emission light 15 from the imaging area as in a case where the object has no crack defects. In addition, another part of the diffused light 14 from the illuminated area 12 is reflected by the crack defect 9, so that it reaches the imaging area 11. Thus the intensity of the diffusion emission light 15 emitted from the imaging area 11 increases, compared with a case where the object has no crack defects.

As described above, since the index of refraction differs across a crack surface, defining a crack defect, the crack surface transmits part of diffused light and reflects another part.

Figure 4:
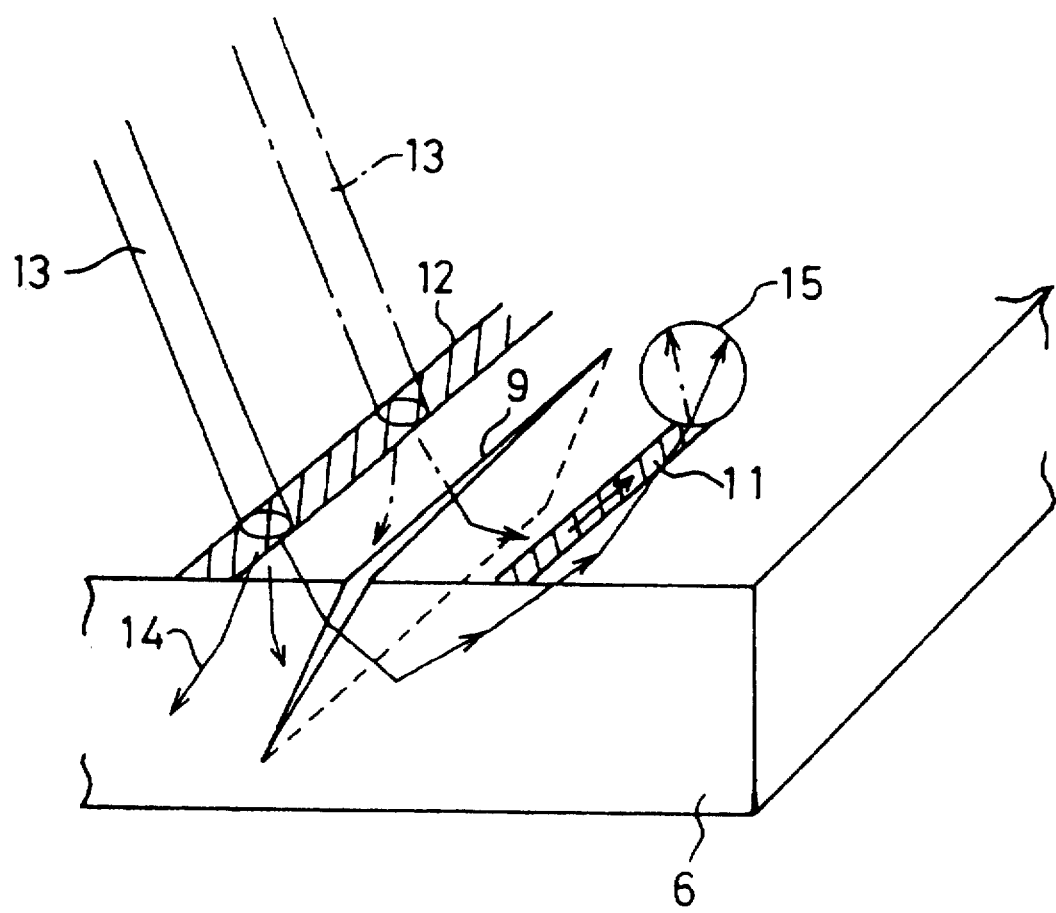
FIG. 4 is a schematic view illustrating a crack defect in an auxiliary scanning direction in an inspected object in an arrangement of the first embodiment.

Taking the foregoing into account, below is described a method of detecting the crack defect 9 in the auxiliary scanning direction in FIG. 4. As shown in FIG. 1, the crack defect 9 in the auxiliary scanning direction is on the right of the object 6. By way of example, using FIG. 5, a situation is dealt with where the stage 5, carrying the object 6, is gradually moved to the left to image the object.

According to the method, the object 6 in FIG. 5a is imaged from left to right by the line sensor 4. The while, the crack defect 9 in the auxiliary scanning direction in the object 6 passes through the imaging area 11. FIG. 5b shows how an imaging signal changes at a pixel on the line sensor 4 as the crack defect 9 moves through the imaging area 11. Consider imaging areas A, B, and C on the object 6. Imaging area A is not affected by the crack defect 9, and thus the imaging signal received by the line sensor 4 is at a reference level without being affected by the crack defect 9. As shown in FIG. 3, the diffusion emission light 15 from imaging area B includes light reflected by a crack surface. Thus the level of the signal received by the line sensor 4 increases with increasing intensity of the diffusion emission light 15. The diffusion emission light 15 from imaging area C is reduced in intensity because it passes through crack surfaces, as shown in FIG. 2. Accordingly, the level of the signal received by the line sensor 4 decreases.

In FIG. 5, the crack defect 9 is near an imaging area, not therein, as in the case of imaging areas B and C, the level of the signal received by the line sensor varies.

Since the signal characteristic described above depends on the size and direction of crack surfaces defining the crack defect 9 in the object 6, the signal level certainly changes even if the opening of the crack defect 9 is on the order of submicrons. Thus imaging means with a pixel resolving power of a few microns to tens of microns can detect a defect. The pixel resolving power is the size of a pixel of the line sensor 4 divided by the magnification of the imaging system. Because even low-magnification imaging means whose pixel resolving power value is larger than the size of the crack defect 9 to be detected can detect the crack defect 9 whose size is smaller than the pixel resolving power value, a large area can be inspected at a low magnifying power at a time. Although FIG. 5 illustrates the crack defect 9 that is open at the surface of the object, the signal level changes described above are also true of an internal crack that is not open at the surface of an inspected object.

The signal level most sharply changes when the crack defect 9 passes through the imaging area 11. Thus the defect can be detected, as shown in FIG. 5c, by, for example, differentiating and binarizing the signal in FIG. 5b based on a threshold value 17 using the image processing unit 8.

Below is described an imaging signal which is received by the line sensor 4 when, using light beams whose intensities differ at the surface of the object, the object is illuminated so that the light beams form a dotted line on the object.

Figure 6A:
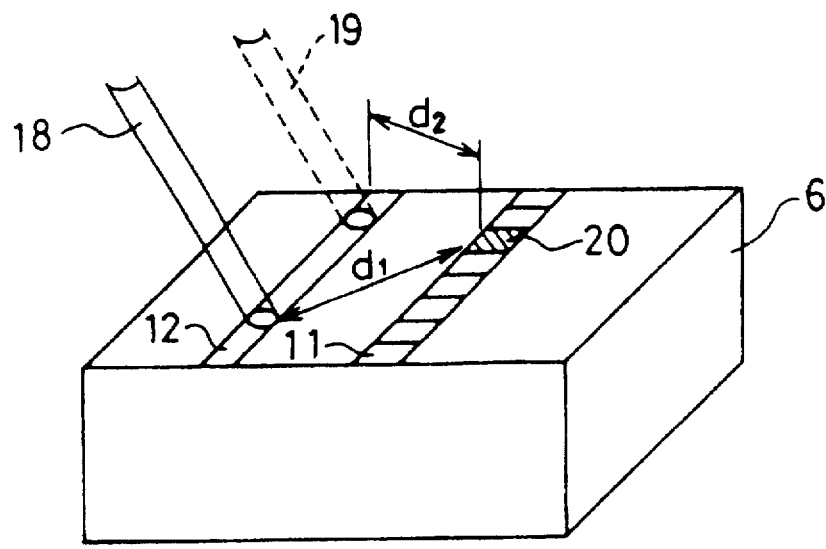
FIGS. 6a, 6b and 6c are schematic views illustrating diffusion emission light generated by illuminating an object in an arrangement of the first embodiment so that light beams form a dotted line dots on the object.
Figure 6B:
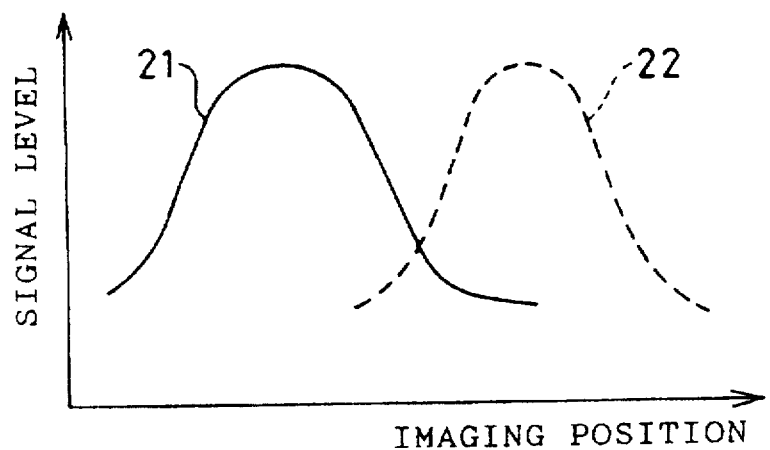
Figure 6C:
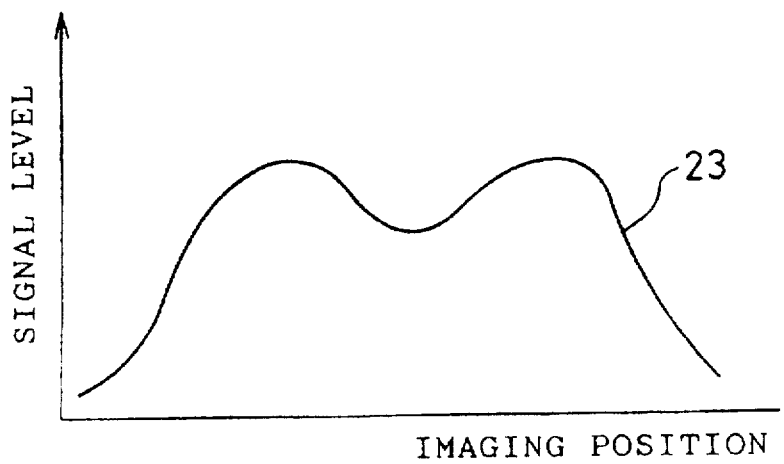

For simplicity, in the arrangement of FIG. 6, spotlight 18 and spotlight 19 are used to illuminate only two locations, that is, form part of a dotted line, on the surface of the object. As part of spotlight 18 and spotlight 19 enters the object 6, it bends and then diffuses through the object 6, while attenuating exponentially. After reaching the imaging area 11, part of the diffused light is emitted from the surface of the object 6 as the diffusion emission light 15. Consider that d1 is the distance between an imaged point 20 from which the line sensor 4 receives an optical signal and the dot formed by the spotlight 18 on the surface of the object and that d2 is the distance between the imaged point 20 and the dot formed by the spotlight 19 on the surface of the object. In general d1 and d2 differ. Thus assuming that the spotlight 18 and spotlight 19 generate imaging signals 21 and 22 received by the line sensor 4, respectively, the level of the signals is as shown in FIG. 6b. One of the curves in FIG. 6b can be translated in the auxiliary scanning direction to align with the other. Since the signal actually received by the line sensor 4 is provided by adding the signals 21 and 22 together, the graph of the level of the resulting signal gently curves as shown in FIG. 6c. Thus an imaging signal which is received by the line sensor when the object is illuminated so that light beams form a dotted line on the object has a gently curved waveform.

Figure 7:
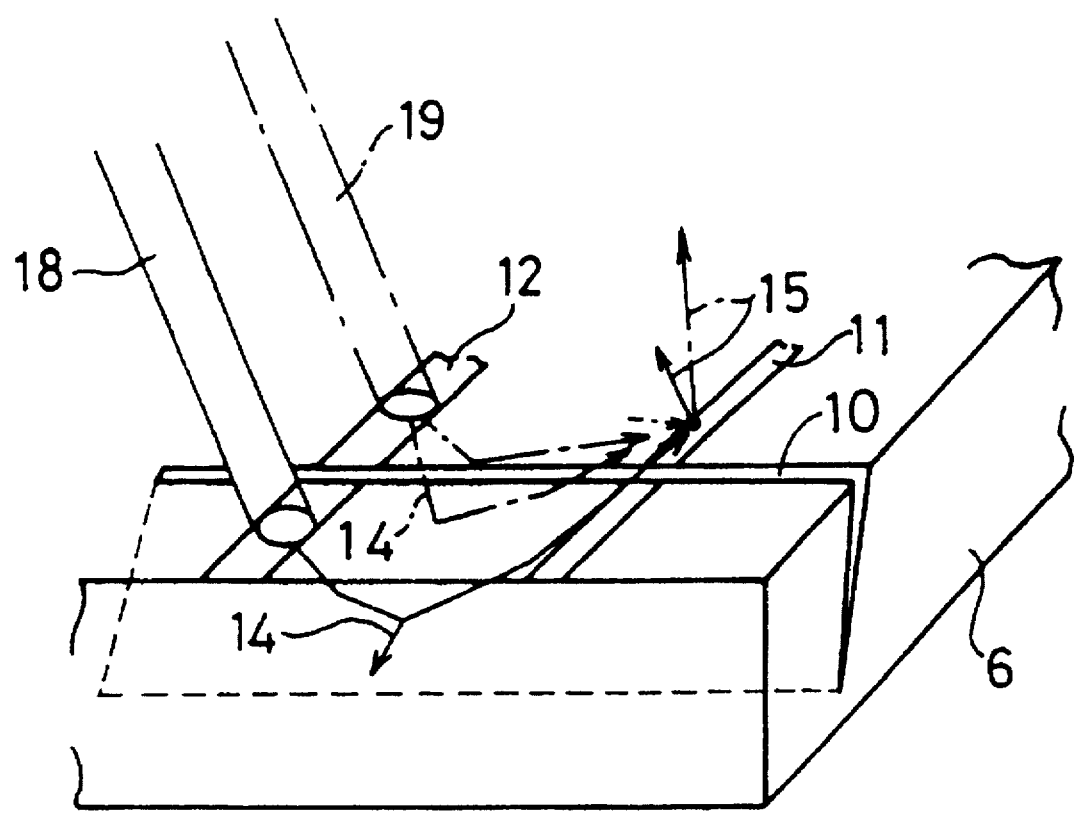
FIG. 7 is a schematic view illustrating a crack defect in a main scanning direction in an object in an arrangement of the first embodiment.

Based on the foregoing, below is described a method of detecting a crack defect 10 in the main scanning direction, shown in FIG. 7. The crack defect 10 is on the right of the object 6 in FIG. 1. Taken as an example is a situation where the stage 5, carrying the object 6 which is illuminated by the illuminating means so that light beams form a dotted line on the object, is moved to the left, as shown in FIG. 8.

Figure 8A:
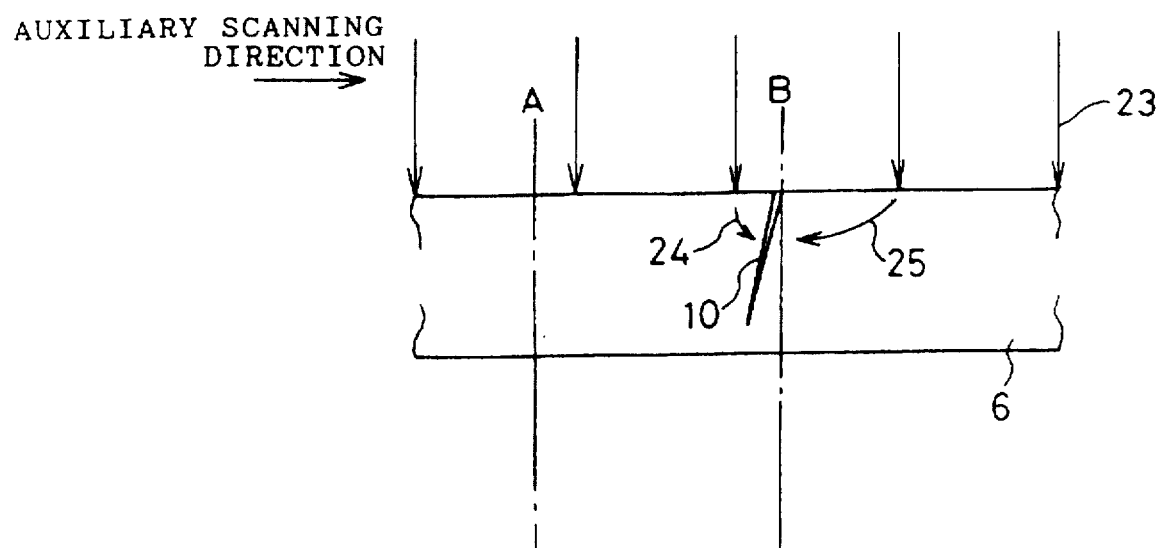
FIGS. 8a, 8b and 8c are schematic views illustrating a signal indicating that a crack defect in a main scanning direction has been detected in an arrangement of the first embodiment.
Figure 8B:
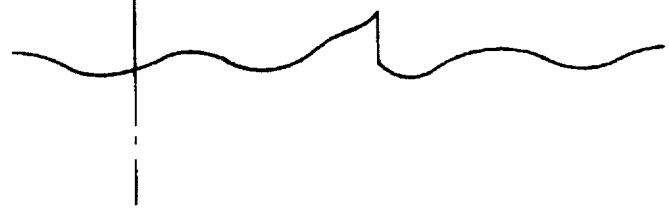

By the method, the object 6 in FIG. 8a, illuminated by light beams 23 arranged so that they form a dotted line on the surface of the object, is imaged using the line sensor 4, while the stage 5 is being moved in the direction perpendicular to the page. FIG. 8b shows changes in the level of an imaging signal received by the line sensor 4 which are observed when the crack defect 10 in the main scanning direction is passing through the imaging area 11. Consider imaging areas A and B on the object 6. Since imaging area A is not affected by the crack defect 10, the imaging signal received by the line sensor 4 is not affected by the crack defect, either, so that the graph of the level of the imaging signal gently curves as described referring to FIG. 6. Diffused light 24, reaching the crack defect 10 in imaging area B from the left, and diffused light 25, reaching the crack defect 10 from the right, generally differ in terms of diffusing distance, since the object is illuminated so that light beams form a dotted line on the object. Because the intensity of diffused light exponentially decreases with increasing diffusing distance, the diffused light 24 and diffused light 25 differ in intensity. Since the index of refraction differs across a crack surface defining a crack defect, thus transmitting part of light diffused through the object 6 and reflecting another part, the difference between the diffused light 24 and the diffused light 25 is kept, so that light diffusion at the crack defect 10 in the object 6 locally becomes discontinuous. As a result, the intensity of diffusion emission light to change, thus sharply changing the imaging signal received by the line sensor 4.

Figure 8C:
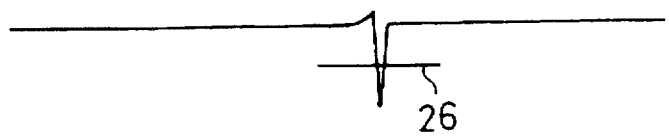

For example, differentiating the signal, whose level changes are shown in FIG. 8b, using the image processing unit 8 causes only the part of the signal level curve corresponding to the crack defect 10 to be emphasized and gently curved parts to be virtually flattened. Binarizing the differentiated signal by setting a threshold value 26 allows the crack defect to be detected as shown in FIG. 8c.

Generally, a crack defect occurs in an undetermined direction. However, a crack in any direction can be detected by the method of detecting the crack defect 9 in the auxiliary scanning direction or the crack defect 10 in the main scanning direction.

If unlike the present invention, light beams of equal intensity is used to illuminate an object so that the beams form a line on the object, the diffused light 24, reaching one crack surface defining the crack 10 from the right, and the diffused light 25, reaching the other from the left, have the same intensity. Thus even if the crack defect 10 transmits part of light diffused through the object 6 and reflects another part, light diffusion does not locally become discontinuous, since the diffused light from the right and the diffused light from the left have the same intensity as described above. Thus the crack defect 10 in the main scanning direction is difficult to detect, because the imaging signal does not remarkably changes.

Detecting changes in the diffusion emission light 15 does not need special highly sensitive detecting equipment. That is, a commercially available CCD imaging apparatus and a display allow the position of a crack defect to be sharply indicated on a display. In the first embodiment, the line sensor 4 is used which has CCD elements disposed in a line, but the CCD elements may be replaced with another type of imaging elements.

Second Embodiment

Figure 9:
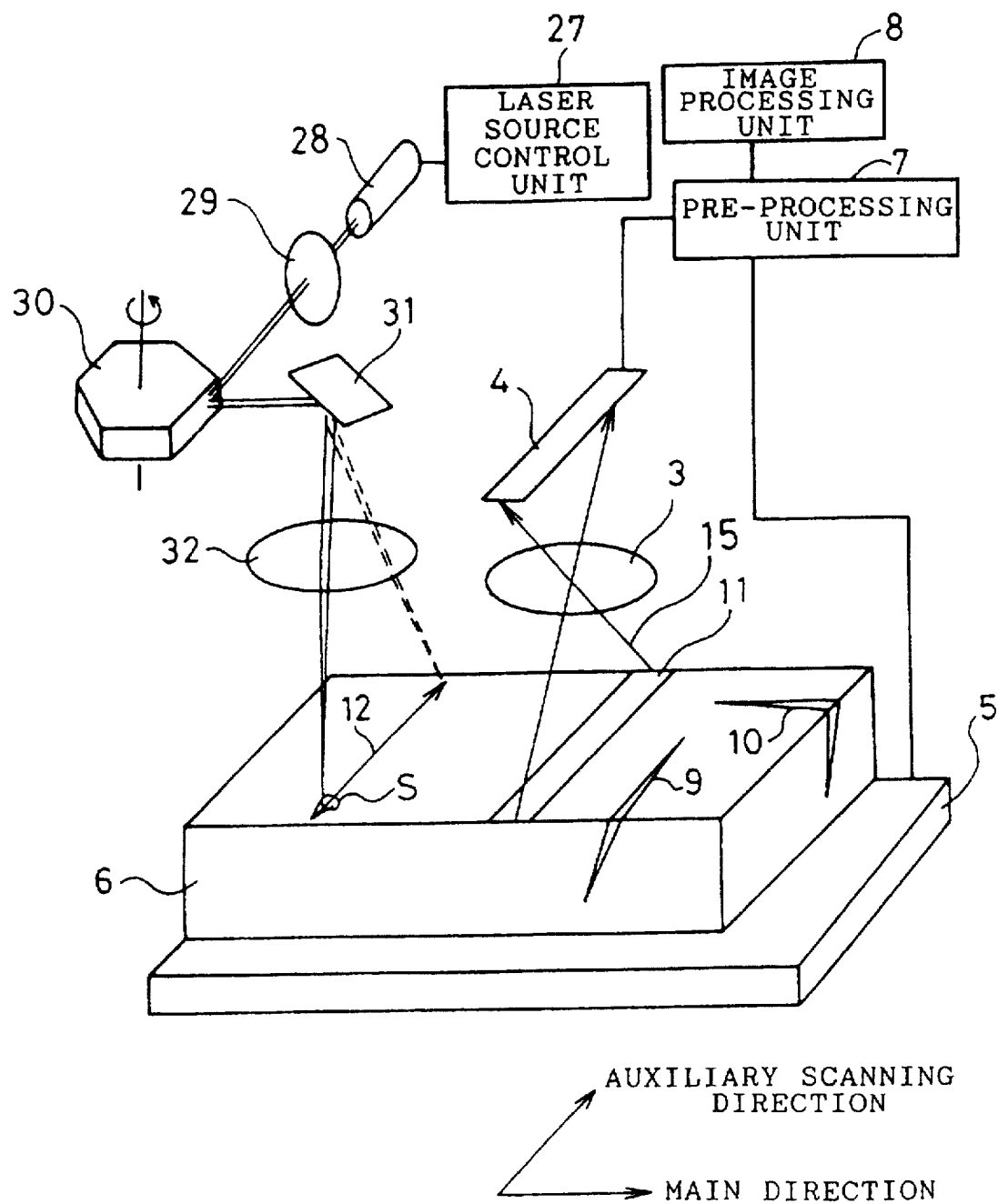
FIG. 9 is a block diagram of an apparatus using an optical method of detecting a defect, which apparatus carries out a second embodiment of the present invention.

FIG. 9 shows an arrangement of an optical defect detecting apparatus according to the second embodiment of the present invention. Components common to FIGS. 1 and 9, which are indicated by the same numerals, are not described below.

Instead of using the illuminating means according to the first embodiment, the optical defect detecting apparatus according to the second embodiment uses illuminating means that one-dimensionally scans the object 6, while changing the intensity of light.

The illuminating means according to the second embodiment consists of a laser source control unit 27, a laser source 28, a collimating lens 29, a polygonal mirror 30, a reflector 31, and a projecting lens 32.

In the above arrangement, laser beams from the laser source 28 are made parallel to each other by the collimating lens 29 and projected on the object 6 by the polygonal mirror 30, reflector 31, and projecting lens 32 to form a spot S. The polygonal mirror 30 is turned to move the focus spot S in the auxiliary scanning direction. During auxiliary scanning, the intensity of laser beams is changed using the laser source control unit 27, and the spot S is moved across the object more than once within the time of exposure of the line sensor 4 to form an illuminated area 12, i.e., a dotted line, for imaging at the line sensor 4.

After entering the object 6, laser light is emitted from the surface of the object 6 as diffusion emission light 15, which contains information on the inside of the object 6. The diffusion emission light 15, diffused from the illuminated area 12 through the object 6 and emitted from the imaging area 11, is projected through an objective lens 3 on the line sensor 4.

Processing an image signal, fed through the pre-processing unit 7 to the image processing unit 8, while gradually moving the stage 5 carrying the object 6 allows crack defects in all directions, including the crack defect 9 in the auxiliary scanning direction and the crack defect 10 in the main scanning direction, to be detected as in the first embodiment.

The simplest way to detect the diffusion emission light 15, emitted from the object 6, in the second embodiment as in the first embodiment is by arranging the illuminated area 12, i.e., a dotted line, in parallel with the imaging area 11, i.e., a line, with an interval between both areas, so that the two areas do not overlap. This arrangement prevents reflected light of high intensity from the illuminated area 12 to enter the line sensor 4 by accident, thus allowing only the diffusion emission light 15 of low intensity to be detected.

In the second embodiment, the laser source is controlled to change the intensity of laser light, but another way may be used for that purpose.

Third Embodiment

Figure 10:
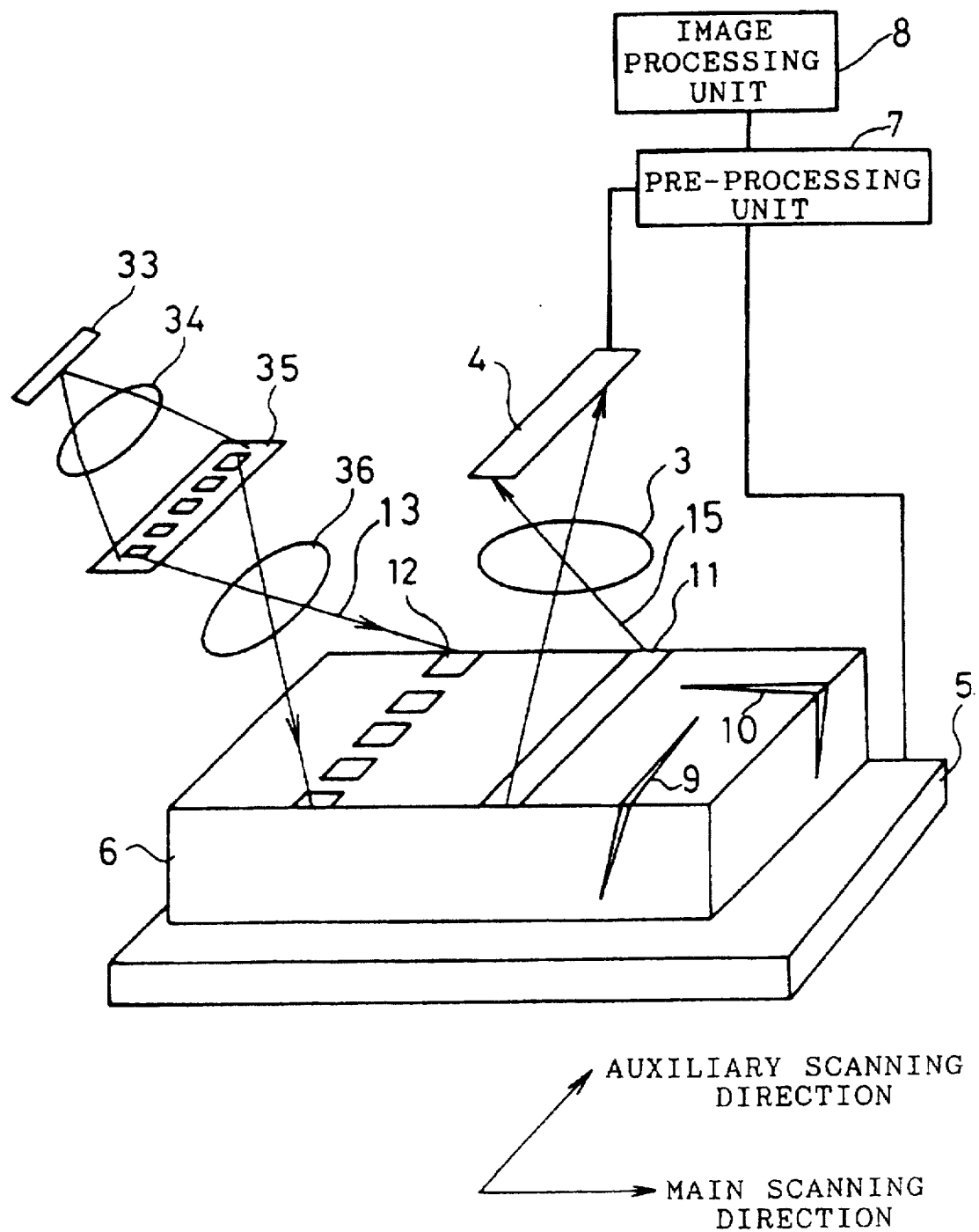
FIG. 10 is a block diagram of an apparatus using an optical method of detecting a defect, which apparatus carries out a third embodiment of the present invention.

FIG. 10 shows an arrangement of an optical defect detecting apparatus according to the third embodiment of the present invention. Components common to FIGS. 1 and 9, which are indicated by the same numerals, are not described below.

Instead of using the illuminating means according to the first embodiment, the optical defect detecting apparatus according to the third embodiment uses illuminating means that illuminates the object 6 by projecting light through slits in a line.

The illuminating means in figure consists of a white light source 33, a condenser lens 34, a slit plate 35 having slits disposed in a line, and a projecting lens 36.

In the above arrangement, light from the white light source 33 illuminates through the condenser lens 34 the slit plate 35 having slits disposed in a line, and then part of the light, passing through the slits, is projected on the object 6 by the projecting lens 36 to illuminate the object 6 using light beams 13 of different intensities so that they form a dotted line. The light beams 13 enter the object 6. The diffusion emission light, emitted from the object 6, contains information on the inside of the object 6. The diffusion emission light 15, diffused from the illuminated area 12 through the object 6 and emitted from the imaging area 11, is focused through the objective lens 3 on the line sensor 4.

Processing an image signal, fed through the pre-processing unit 7 to the image processing unit 8, while gradually moving the stage 5 carrying the object 6 allows crack defects in all directions, including the crack defect 9 in the auxiliary scanning direction and the crack defect 10 in the main scanning direction, to be detected as in the first embodiment.

The simplest way to detect the diffusion emission light 15, emitted from the object 6, in the third embodiment as in the first embodiment is by arranging the illuminated area 12, i.e., a dotted line, in parallel with the imaging area 11, i.e., a line, with an interval between both areas, so that the two areas do not overlap. This arrangement prevents reflected light of high intensity from the illuminated area to enter the line sensor 4 by accident, thus allowing only the diffusion emission light 15 of low intensity to be detected.

Fourth Embodiment

Figure 11:
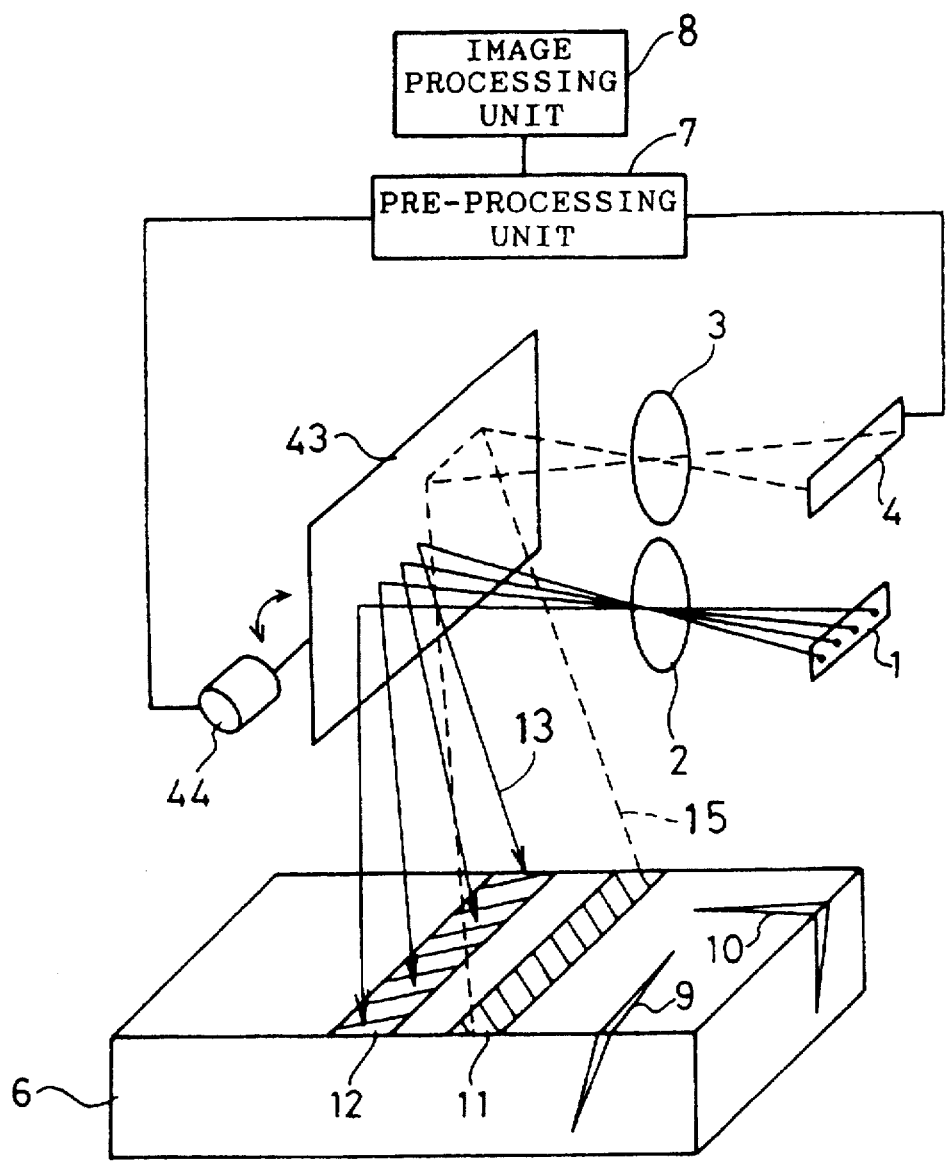
FIG. 11 is a block diagram of an apparatus using an optical method of detecting a defect, which apparatus carries out a fourth embodiment of the present invention.

FIG. 11 shows an arrangement of an optical defect detecting apparatus according to the fourth embodiment of the present invention. Components common to FIGS. 1 and 11, which are indicated by the same numerals, are not described below.

Instead of the illuminating means and imaging means of the first embodiment, the optical defect detecting apparatus according to the fourth embodiment uses illuminating means that illuminates the object 6 throughout a reflector so that light beams form a dotted line and imaging means that detects through the reflector light emitted from a linear area parallel to the illuminated area formed on the object 6 by the above-described illuminating means. The optical defect detecting means according to the fourth embodiment also uses drive means that rotates the reflector back and forth by a predetermined angle, not the drive means of the first embodiment.

The illuminating means of the fourth embodiment consists of the array light source 1, projecting lens 2, and a reflector 43.

The imaging means of the fourth embodiment consists of the reflector 43, objective lens 3, and line sensor 4.

The drive means of the fourth embodiment consists of a reflector rotating drive unit 44 rotating the reflector 43 back and forth by the predetermined angle.

The pre-processing unit 7 produces an image using a signal from the line sensor 4 and a reflector rotating signal from the reflector rotating drive means 44.

In the above arrangement, light beams from the array light source 1 are projected through the projecting lens 2 and reflector 43 on the object 6 to illuminate the object so that the beams, differing in intensity at the surface of the object, form a dotted line on it. The light beams 13 enter the object 6. The diffusion emission light 15, emitted from the object 6, contains information on the inside of the object 6. The diffusion emission light 15, diffused from the illuminated area 12 through the object 6 and emitted from the imaging area 11, is reflected by the reflector 43 of the imaging means and focused through the objective lens 3 on the line sensor 4.

Processing an image signal, fed through the pre-processing unit 7 to the image processing unit 8, while gradually moving the illuminated area 12 and imaging area 11 on the object 6 by rotating the reflector 43 using the reflector rotating drive unit 44 allows crack defects in all directions, including the crack defect 9 in the auxiliary scanning direction and the crack defect 10 in the main scanning direction, to be detected as in the first embodiment.

The simplest way to detect the diffusion emission light 15 containing information on the inside of the object 6, which light is emitted from the object 6, in the fourth embodiment as in the first embodiment is by arranging the illuminated area 12, i.e., a dotted line, in parallel with the imaging area 11, i.e., a line, with an interval between both areas, so that they do not overlap. This arrangement prevents reflected light of high intensity from the illuminated area to enter the line sensor 4 by accident, thus allowing only the diffusion emission light 15 of low intensity to be detected.

Unlike the first embodiment described referring to FIG. 1, the fourth embodiment does not need the stage 5. Thus its structure is relatively simple. When coupled with the second and third embodiments, whose arrangements are shown in FIGS. 9 and 10, respectively, a method in which the reflector 43 is rotated to simultaneously move the illuminated area 12 and imaging area 11 eliminates the stage 5.

Fifth Embodiment

Figure 12:
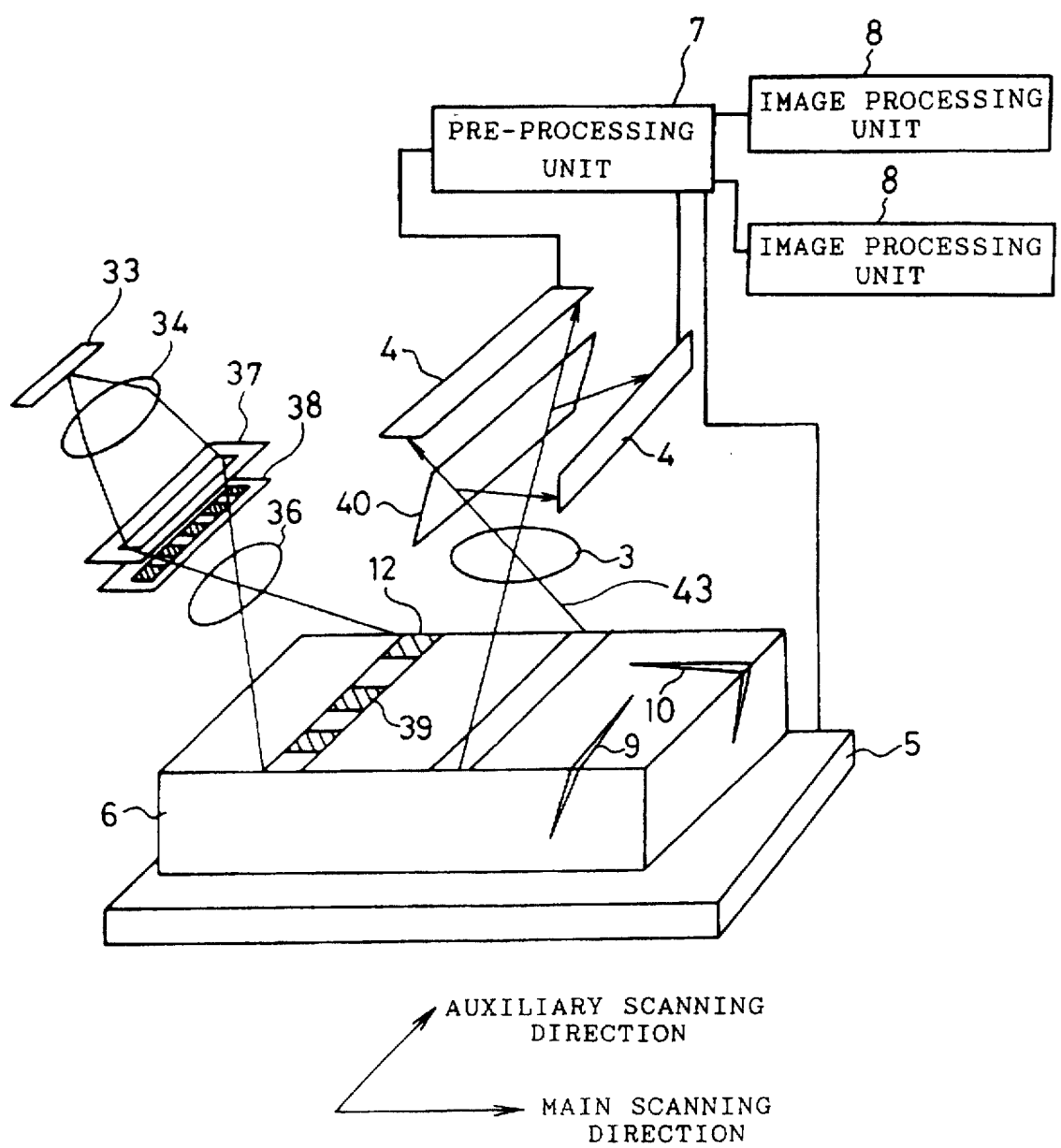
FIG. 12 is a block diagram of an apparatus using an optical method of detecting a defect, which apparatus carries out a fifth embodiment of the present invention.

FIG. 12 shows an arrangement of an optical defect detecting apparatus according to the fifth embodiment of the present invention. Components common to FIGS. 1 and 12, which are indicated by the same numerals, are not described below.

Instead of the illuminating means and imaging means of the first embodiment, the optical defect detecting apparatus according to the fifth embodiment uses illuminating means that projects light beams, composed of light rays belonging to a plurality of wavelength bands, on the object without letting the beams interfere with each other so that they differ in intensity at the surface of the object and chromatic resolving imaging means of wavelength separation type that separates into wavelength bands light rays emitted from the linear area parallel to the illuminated area when detecting the light.

The illuminating means of the fifth embodiment consists of the white light source 33, condenser lens 34, a slit plate 37 with openings disposed in a line, a band-pass filter 38 with zones alternately disposed which transmit only light belonging to wavelength band a and only light belonging to wavelength band b, and the projecting lens 36.

The chromatic resolving imaging means of the fifth embodiment consists of the objective lens 3, a dichroic mirror 40 that transmits light belonging to wavelength band a and reflects light belonging to wavelength band b, and two line sensors 4, one receiving light belonging to wavelength band a and the other receiving light belonging to wavelength band b.

The pre-processing unit 7 of the image processing means produces an image using signals from the two line sensors 4 and a moving signal from the stage 5, carrying the object 6 and outputs the signal for the image to two image processing units 8, one for wavelength band a and the other for wavelength band b.

In the above arrangement, light from the white light source 33 illuminates through the condenser lens 34 the slit plate 37 having openings disposed in a line, and then part of the light, passing through the openings, is projected on the object. When the object is illuminated, the band-pass filter 38 with zones alternately disposed which transmit only light belonging to wavelength band a and only light belonging to wavelength band b project light beams 39 which form a linear illuminated area having zones alternately placed which are illuminated by only light belonging to wavelength band a and by only light belonging to wavelength band b.

The light beams 39 enter the object 6, the beams being composed of only light belonging to wavelength band a and of only light belonging to wavelength band b. Diffusion emission light 43, emitted from the object 6, contains information on the inside of the object 6. The diffusion emission light 43, diffused from the illuminated area 12 through the object 6 and emitted from the imaging area 11, enters the objective lens 3 of the imaging means. Then the dichroic mirror 40 transmits light belonging to wavelength band a and reflects light belonging to wavelength band b. The line sensors 4 are placed at the positions where light belonging to wavelength band a and light belonging to wavelength band b form images.

Processing an image signal for each wavelength band, fed through the pre-processing unit 7, forming an image from signals from the two line sensors 4 and a signal from the stage 5, to the image processing unit 8, while gradually moving the stage 5 bearing the object 6 allows crack defects in all directions, including the crack defect 9 in the auxiliary scanning direction and the crack defect 10 in the main scanning direction, to be detected as in the first embodiment.

The simplest way to detect the diffusion emission light 43 containing information on the inside of the object 6, which light is emitted from the object 6, in the fifth embodiment as in the first embodiment is by arranging on the object 6 the linear illuminated area 12 with zones alternately placed which are illuminated with only light belonging to wavelength band a and with only light belonging to wavelength band b on the one hand and the linear imaging area 11 on the other in parallel with each other, with an interval between both areas, so that the imaging area 11, from which the diffusion emission light 43 is received, and the illuminated area do not overlap. This arrangement prevents reflected light of high intensity from the illuminated area to enter the line sensors 4 by accident, thus allowing only the diffusion emission light 43 of low intensity to be detected.

A detection procedure is described below, for example, for the crack defect 9 in the auxiliary scanning direction and the crack defect 10 in the main scanning direction, which defects are at right angles to each other, as representatives of crack defects in various directions.

Based on the foregoing, below is described a method of detecting the crack defect 9 in the auxiliary scanning direction. The crack defect 9 is on the right of the object 6 in FIG. 12. FIG. 13 shows a case where the stage 5, carrying the object 6, is moved to image the object.

By the method, the object 6 in FIG. 13a is imaged from left to right by the two line sensors 4. The while, the crack defect 9 in the auxiliary scanning direction in the object 6 passes through the imaging area 11. How an imaging signal changes at a pixel on the line sensor 4 as the crack defect 9 moves through the imaging area 11 is illustrated in FIG. 13b for wavelength band a and in FIG. 13d for wavelength band b. The changes are almost the same for wavelength band a and wavelength band b. The imaging signal changes in the same manner as the crack detection signal, described referring to FIG. 5. Thus the defect can be detected, as shown in FIG. 13c and 13e, by, for example, differentiating and binarizing the signal in FIG. 5b based on a threshold value 17 using the image processing unit 8.

Below is described a method of detecting the crack defect 10 in the main scanning direction. The crack defect 10 is on the right of the object 6 in FIG. 12. Taken as an example is a situation where the stage 5, carrying the object 6 which is illuminated by the illuminating means so that light beams form a dotted line on the object, is moved to the left, as shown in FIG. 14.

Figure 14A:
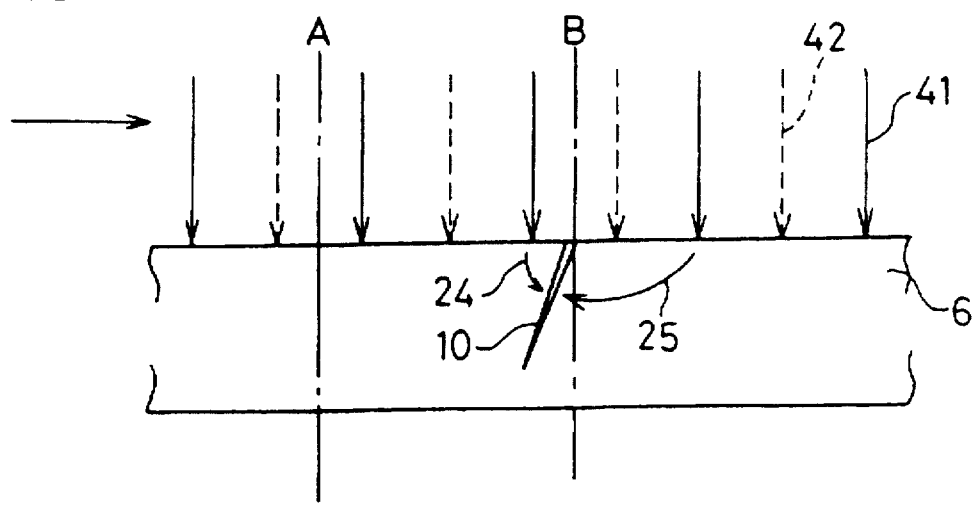
FIGS. 14a, 14b, 14c, 14d, 14e and 14f are schematic views illustrating a signal indicating that a crack defect in a main scanning direction has been detected in an arrangement of the fifth embodiment.

By the method, the object 6 in FIG. 14a, illuminated by light beams 41, composed of light rays belonging to wavelength band a and arranged so that the beams form a dotted line, and by light beams 42, shown in broken lines, is imaged for each wavelength band using the two line sensors 4, while the stage 5 is being moved in the direction perpendicular to the page. Changes in the level of imaging signals received by the line sensors 4, which changes are observed when the crack defect 10 in the main scanning direction is passing through the imaging area 11, are shown in FIG. 14b for wavelength band a and in FIG. 14d for wavelength band b.

For wavelength band a, consider imaging areas A and B on the object 6. Since imaging area A is not affected by the crack defect 10, the imaging signal received by the line sensors 4 is not affected by the crack defect, either, so that the graph of the level of the imaging signal gently curves as described referring to FIG. 8. The diffused light 24, reaching the crack defect 10 in imaging area B from the left, and the diffused light 25, reaching the crack defect 10 from the right, generally differ in terms of diffusing distance, since the object is illuminated so that light beams form a dotted line on the object. Because the intensity of diffused light exponentially decreases with increasing diffusing distance, the diffused light 24 and diffused light 25 differ in intensity. Since the index of refraction differs across a crack surface defining a crack defect, thus transmitting part of light diffused through the object 6 and reflecting another part, the difference between the diffused light 24 and the diffused light 25 is kept, so that light diffusion at the crack defect 10 in the object 6 locally becomes discontinuous. As a result, the intensity of the diffusion emission light 43 changes, thus remarkably reducing the level of the imaging signal received by the line sensor 4 for wavelength band a, as shown in FIG. 14b.

The light beams composed of light rays belonging to wavelength band a and those composed of light rays belonging to wavelength band b illuminate different locations. Thus the intensity difference relationship between the diffused light 24, reaching the crack defect 10 from the left, and the diffused light 25, reaching the crack defect 10 from the right, is reversed for wavelength bands a and b. As a result, the level of the imaging signal received by the line sensor 4 for wavelength band a sharply increases, as shown in FIG. 14d.

Figure 14B:
Figure 14C:
Figure 14D:
Figure 14E:
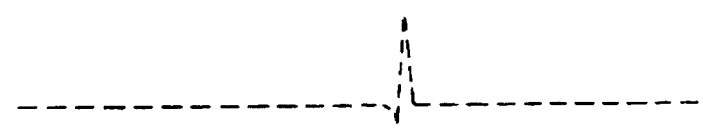

For example, differentiating the signal, whose level changes are shown in FIG. 14b and 14d, using the image processing unit 8 causes only the part of the signal level curve corresponding to the crack defect 10 to be emphasized and gently curved parts to be virtually flattened, as shown in FIG. 14c for wavelength band a and in FIG. 14e for wavelength band b.

Figure 14F:
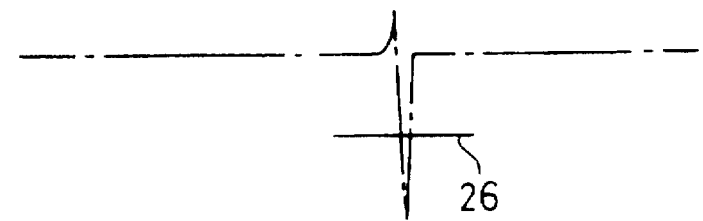

When differential of these two signals is determined, gives a signal of FIG. 14f, thus improving the sensitivity of detection of the crack defect 10. Binarizing the differentiated signal by setting a threshold value 26 allows the crack defect to be detected.

In the fifth embodiment, light beams composed of light rays belonging to two wavelength bands. However, light beams composed of light rays belonging to two wavelength bands or more may be used for illuminating an inspected object. Moreover, in the fifth embodiment, the white light source 33, slit plate 37, and band-pass filter 38 are used to form light beams composed of light rays belonging to a plurality of wavelength bands. Alternatively, a plurality of light sources producing light rays belonging to different wavelength bands, such as lasers and LEDs, may be used to arrange illuminating means, or spot light beams differing in wavelength band may be used to arrange scanning-type illuminating means, as in the fourth embodiment described referring to FIG. 9.

According to the first to fifth embodiments, changes in the intensity of the diffusion emission light 15 or 43, diffused from the limited illuminated area 12 to the imaging area 11 and emitted from the surface of the object 6, due to a crack defect in the imaging area 11 or thereabouts are used to detect the defect by emphasizing a signal part corresponding to it. Thus a crack detect can be detected which has an opening smaller than the value of the resolving power of the imaging means. This provides an inexpensive defect detecting apparatus that can fast detect a surface crack defect or an internal crack defect of the object 6 with high accuracy no matter whether the object diffuses light or not.

Sixth Embodiment

Figure 15:
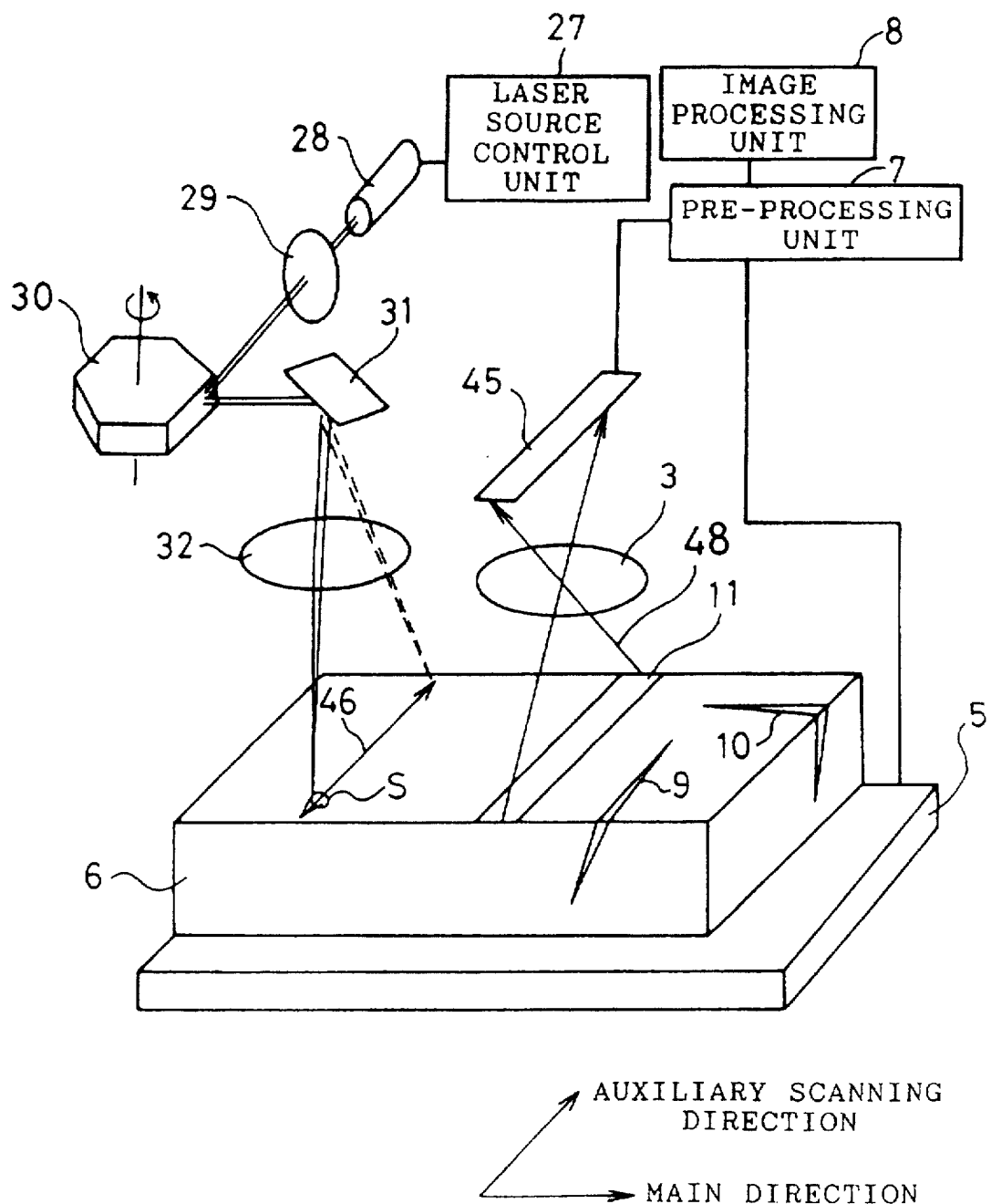
FIG. 15 is a block diagram of an apparatus using an optical method of detecting a defect, which apparatus carries out a sixth embodiment of the present invention.

FIG. 15 shows an arrangement of an optical defect detecting apparatus according to the sixth embodiment of the present invention. Components common to FIGS. 1 and 15, which are indicated by the same numerals, are not described below.

Instead of using the illuminating means according to the first embodiment, the optical defect detecting apparatus according to the second embodiment uses heating means that one-dimensionally scans the object 6, while changing the intensity of projected light to heat the object and imaging means that detects infrared rays emitted from a linear area parallel to a heated area illuminated by the heating means.

Using a signal from the imaging means, the image processing means detects a portion of the object 6 which is unhomogeneous in terms of heat conduction.

The heating means according to the sixth embodiment consists of the laser source control unit 27, laser source 28, collimating lens 29, polygonal mirror 30, reflector 31, and projecting lens 32.

The imaging means according to the sixth embodiment consists of the objective lens 3 and a line sensor 45 for detecting infrared rays.

In the above arrangement, laser beams from the laser source 28 are made parallel to each other by the collimating lens 29 and projected on the object 6 by the polygonal mirror 30, reflector 31, and projecting lens 32 to form a spot S. The polygonal mirror 30 is rotated to move the projected spot S in the auxiliary scanning direction. During auxiliary scanning, the intensity of laser beams is changed using the laser source control unit 27, and the spot S is moved across the object more than once within the time of exposure of the line sensor 45 to aim laser beams at the object 6 so that the beams form a dotted line on the object. Because the object 6 absorbs the beams to heat, a heated area is formed which includes heated spots in a line.

Heat is conducted into the object 6. When reaching part of the surface of the object 6, heat is emitted as infrared rays from the part. The infrared rays contain information on the inside of the object 6. The emitted rays are called diffusion emission infrared light herein. Diffusion emission infrared rays 48, diffused from the heated area 46 through the object 6 and emitted from the imaging area 11, is projected through the objective lens 3 of the imaging means on the line sensor 45 for detecting infrared rays.

While the object 6 is being moved using the stage 5, an image signal, fed through the pre-processing unit 7, producing an image from a signal from the line sensor 45 and a signal from the stage 5, to the image processing unit 8 is processed to detect a crack defect in the object 6.

In the sixth embodiment, the simplest way to detect the diffusion emission infrared rays 48 from the surface of the object 6, which contain information on the inside of the object 6, is by arranging the heated area 12 with spots, heated by the heating means, in a line and the linear imaging area, from which the imaging means receives light, in parallel with each other, with a separation interval between both areas, so that the imaging area, from which the diffusion emission infrared rays are received, and the heated area 12 do not overlap. This arrangement prevents infrared rays of high intensity from the heated area 46 from entering the line sensor 45 by accident, thus allowing only the diffusion emission infrared rays 48 of low intensity to be detected.

If a portion which is unhomogeneous in terms of heat conduction, that is, a portion at which the thermal conductivity locally changes, is in the object 6, the intensity of infrared rays emitted from part of the object surface near the portion more significantly changes than that of infrared rays from other parts. The reason for this is described below.

Figure 16A:
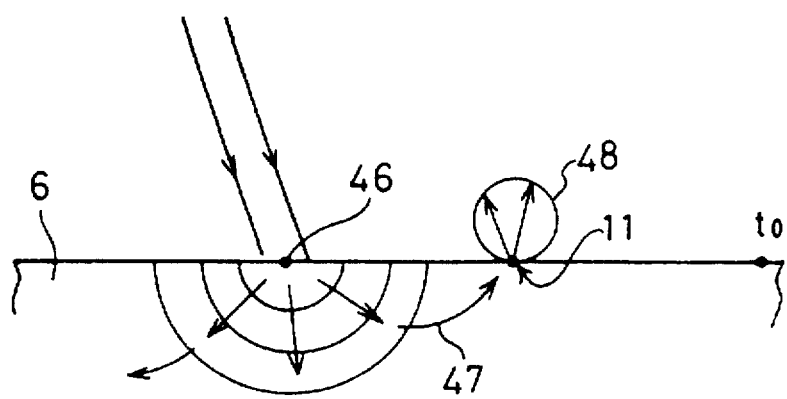
FIGS. 16a and 16b are schematic views illustrating thermal diffusion which occurs when a inspected object has no crack defect in an arrangement of the sixth embodiment.
Figure 16B:
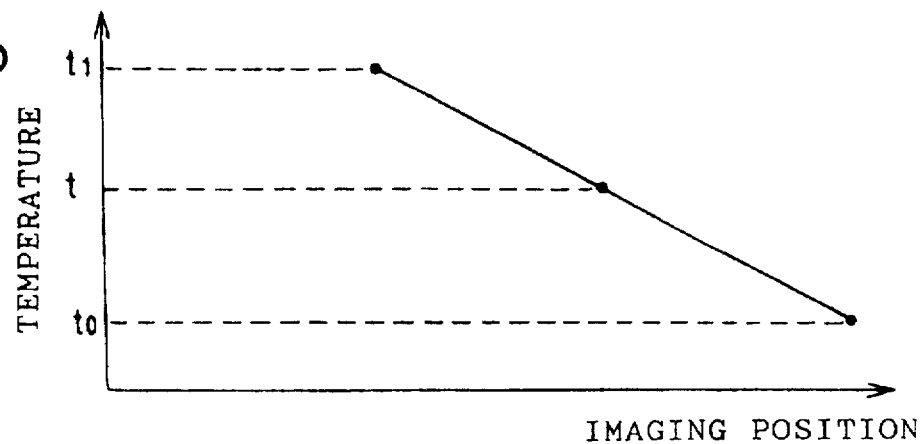

FIG. 16a is a schematic view illustrating a case where part of heat 47, conducted from the heated area on the object 6 and diffused throughout the object, causes the diffusion emission infrared rays 48 to be emitted from the imaging area 11. The temperature distribution over the surface of the object 6 is shown by the graph of FIG. 16b, where t0 is the temperature at the surface of the object 6 as measured before the object is heated, t1 is the temperature in the heated area 46, and t is the temperature in the imaging area 11.

FIG. 17 is a schematic cross-sectional view of the crack defect 9 in the object 6. Part of the heat 47 diffused reaches the imaging area 11 on the object 6, causing the diffusion emission infrared rays 48 to be emitted. As shown in FIG. 17, a cross section of the crack defect 9 is defined by crack surfaces in the object 6, between which the air layer 16 having a much lower thermal conductivity than the thermal conductivity $\lambda$ of the object 6, composed of metal, resin, or the like. Thus the thermal conductivity differs across the interface between a crack and the object, so that the heat 47, diffused through the object 6, becomes nonhomogeneous.

Figure 17A:
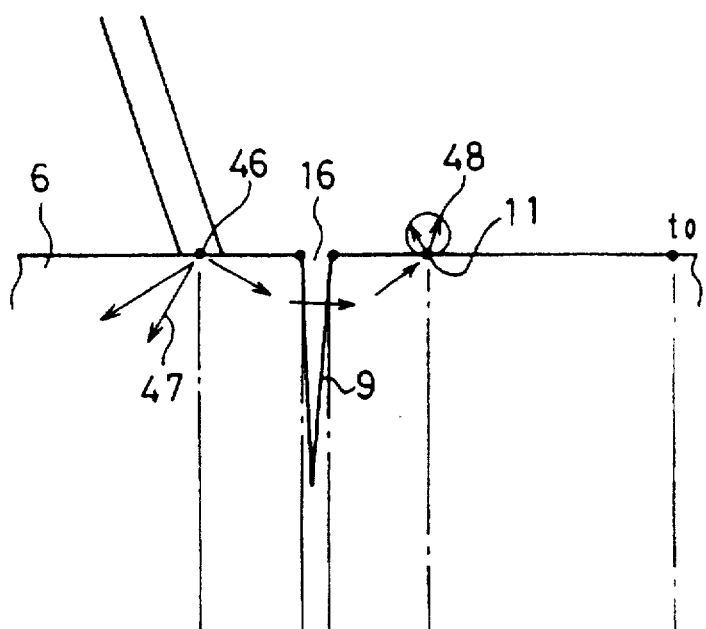
FIGS. 17a and 17b are schematic views illustrating thermal diffusion which occurs when a crack defect is between an illuminated area and an imaging area in an arrangement of the sixth embodiment.
Figure 17B:
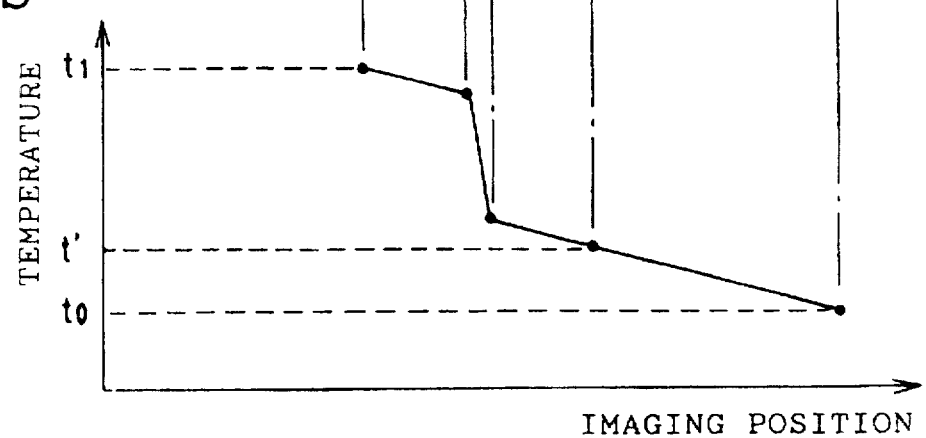

As shown in FIG. 17a, if the crack defect 9 is between the heated area 46 and the imaging area 11, part of the heat 47, diffused through the object 6 and reaching imaging area 11, is conducted by the crack defect 9. Since heat diffusion through the crack defect 9 is shut off by the air layer 16, the amount of heat reaching the imaging area 11 decreases. When the object 6 is heated, the temperature distribution over the surface of the object is as shown in FIG. 17b, where t0 is the temperature at the surface of the object 6 as measured before the object is heated, and t1 is the temperature in the heated area 46. The temperature t' in the imaging area 11 as measured when the crack defect 9 is present is lower than the temperature t as measured when the crack defect 9 is not present. Thus the intensity of the diffusion emission infrared rays emitted from the imaging area 11 becomes lower, compared with a case where the crack defect 9 is not present.

Figure 18A:
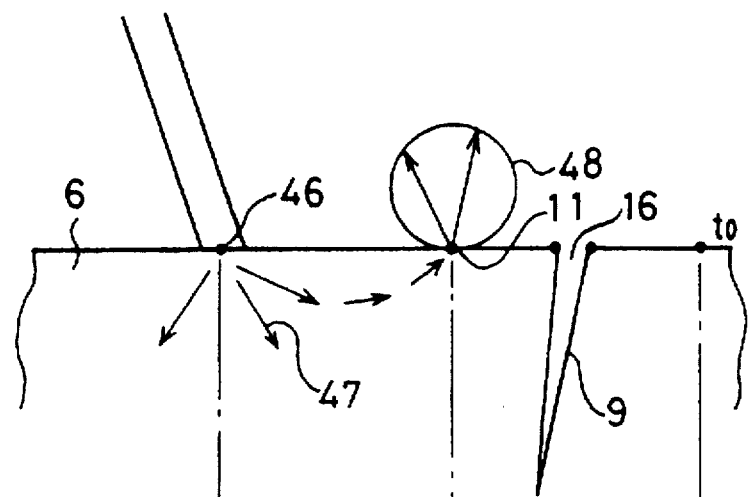
FIGS. 18a and 18b are schematic views illustrating thermal diffusion which occurs when a crack defect is except between an illuminated area and an imaging area in an arrangement of the sixth embodiment.
Figure 18B:
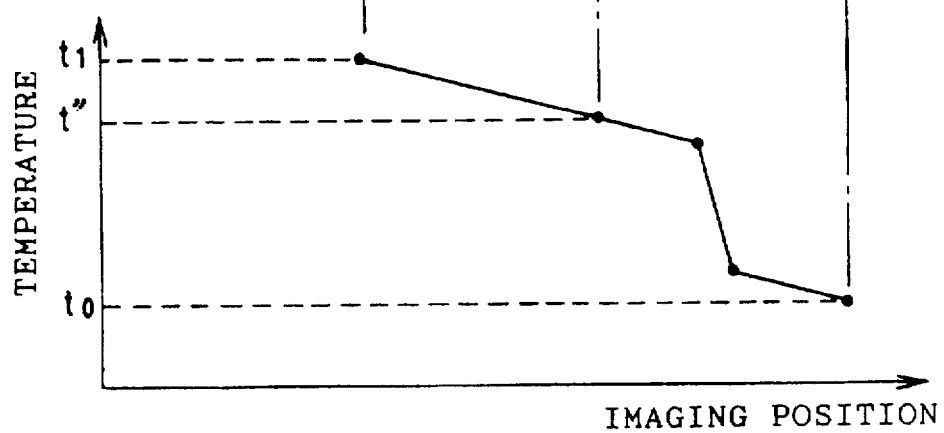

On the other hand, if the crack defect 9 is present except between the heated area 46 and the imaging area 11, part of the heat 47 diffused reaches the imaging area 11 as in a case where no crack defect is present. The crack defect 9 shuts off another part of the heat 47 diffused, so that heat diffusion is inhibited. Thus part of heat diffused by the defect reaches the imaging area 11. When the object 6 is heated, the temperature distribution over the surface of the object is as shown in FIG. 18b, where t0 is the temperature at the surface of the object 6 as measured before the object is heated, and t1 is the temperature in the heated area 46. The temperature t" in the imaging area 11 as measured when the crack defect 9 is present is higher than the temperature t as measured when the crack defect 9 is not present. Thus the intensity of the diffusion emission infrared rays 48 emitted from the imaging area 11 becomes higher, compared with a case where the crack defect 9 is not present.

Since the air layer 16 between crack surfaces, defining a crack defect, causes thermal conductivity difference, the crack defect shuts off part of diffused heat.

Taking the foregoing into account, below is described a method of detecting the crack defect 9 in the auxiliary scanning direction. As shown in FIG. 15, the crack defect 9 in the auxiliary scanning direction is on the right of the object 6. By way of example, using FIG. 19, a situation is dealt with where the stage 5, carrying the object 6, is gradually moved to the left to image the object.

According to the method, the object 6 in FIG. 19a is imaged from left to right by the line sensor 45. The while, the crack defect 9 in the auxiliary scanning direction in the object 6 passes through the imaging area 11. FIG. 19b shows how an imaging signal changes at a pixel on the line sensor 4 as the crack defect 9 moves through the imaging area 11. Consider imaging areas A, B, and C on the object 6. Imaging area A is not affected by the crack defect 9, and thus the imaging signal received by the line sensor 45 is at a reference level without being affected by the crack defect 9. As shown in FIG. 18, the level of the signal received by the line sensor 45 increases with increasing intensity of the diffusion emission infrared rays 48 from imaging area B. The diffusion emission infrared rays 48 from imaging area C is reduced in intensity because it is shut off by the air layer 16 in the crack defect 9, as shown in FIG. 17. Accordingly, the level of the signal received by the line sensor 45 decreases.

The signal characteristic described above depends on the size and direction of the air layer 16 in the crack defect 9. Thus if the crack defect 9 is near an imaging area, not therein, as in the case of imaging areas B and C of FIGS. 19, the level of the signal received by the line sensor varies. Consider that the pixel resolving power is the size of a pixel of the line sensor 45 divided by the magnification of the imaging means. Because even low-magnification imaging means whose pixel resolving power value is larger than the size of the crack defect 9 to be detected can detect the crack defect 9 whose size is smaller than the pixel resolving power value, a large area can be inspected at a low magnifying power at a time. Although FIG. 19 illustrates the crack defect 9 that is open at the surface of the object, the signal level changes described above are also true of an internal crack that is not open at the surface of an inspected object. The signal level most sharply changes when the crack defect 9 passes through the imaging area 11. Thus the defect can be detected, as shown in FIG. 19c, by, for example, differentiating and binarizing the signal in FIG. 19b based on a threshold value 26 using the image processing unit 8.

Below is described an imaging signal which is produced by the line sensor 45 when the heated area 46 like a dotted line is formed. Consider that an imaging point on the line sensor 45. Since the distances between dots formed by light beams in the heated area 46 and the imaging point generally differ, the amount of hear conducted from the dots to the imaging point also differs. Thus a detection signal from the line sensor 46 has a gently curved waveform. Based on the foregoing, below is described a method of detecting the crack defect 10 in the main scanning direction. The crack defect 10 is on the right of the object 6 in FIG. 15. Taken as an example is a situation where the stage 5, carrying the object 6 which is illuminated by the illuminating means so that light beams form a dotted line on the object, is moved to the left, as shown in FIG. 20.

Figure 20A:
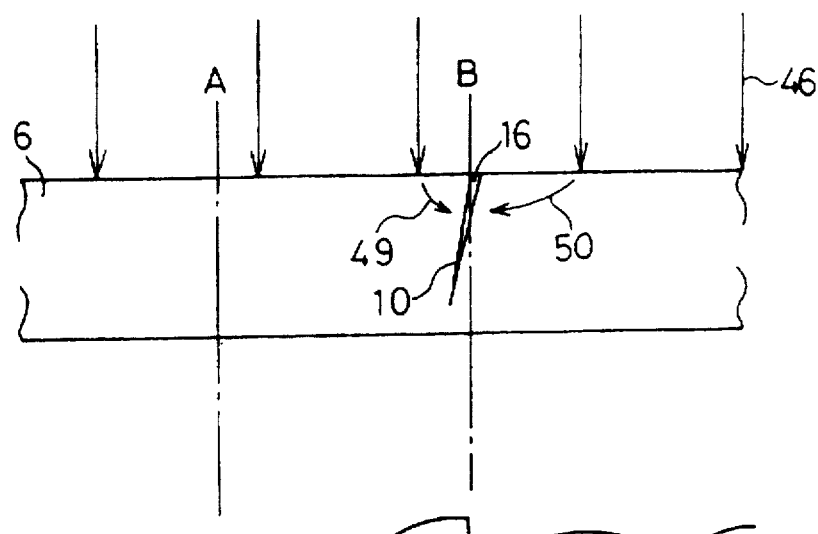
FIGS. 20a, 20b and 20c are schematic views illustrating a signal indicating that a crack defect in a main scanning direction has been detected in an arrangement of the sixth embodiment.
Figure 20B:

By the method, the object 6 in FIG. 20a, on which the heated area 46 is provided so that light beams form a dotted line on the surface of the object, is imaged using the line sensor 45, while the stage 5 is being moved in the direction perpendicular to the page. FIG. 20b shows changes in the level of an imaging signal received by the line sensor 45 which are observed when the crack defect 10 in the main scanning direction is passing through the imaging area 11. Consider imaging areas A and B on the object 6. Since imaging area A is not affected by the crack defect 10, the imaging signal received by the line sensor 45 is not affected by the crack defect 10, either, so that the graph of the level of the imaging signal gently curves. Diffused heat 49, reaching the crack defect 10 in imaging area B from the left, and diffused heat 50, reaching the crack defect 10 from the right, generally differ in terms of diffusing distance, since the heated area 46 is provided so that light beams form a dotted line on the object. Because the amount of heat diffused decreases with increasing diffusing distance, the diffused heat 49 and diffused heat 50 differ in amount. Since the thermal conductivity differs across a crack surface between the air layer 16 in the crack defect 10 and the object, thus shutting off heat diffusion in the object, the difference in amount between the diffused heat 49 and the diffused heat 50 is kept, so that the temperature distribution in the object 6 locally becomes discontinuous. As a result, the intensity of the diffusion emission infrared rays 48 change, thus sharply changing the imaging signal received by the line sensor 45.

Figure 20C:
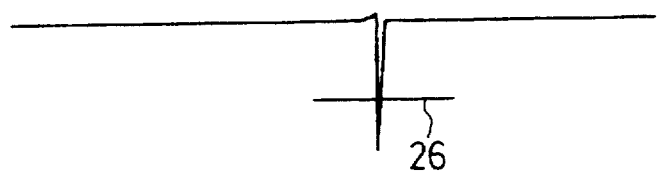

For example, differentiating the signal, whose level changes are shown in FIG. 20b, using the image processing unit 8 causes only the part of the signal level curve corresponding to the crack defect 10 to be emphasized and gently curved parts to be virtually flattened. Binarizing the differentiated signal by setting a threshold value 26 allows the crack defect 10 to be detected as shown in FIG. 20c.

Generally, a crack defect occurs in an undetermined direction. However, a crack in any direction can be detected by the method of detecting the crack defect 9 in the auxiliary scanning direction or the crack defect 10 in the main scanning direction.

If an uniformly linear heated area is provided instead of the heated area 46 like a dotted line, the amount of the diffused heat 49, reaching the air layer 16 in the crack defect 10 from the left, becomes equal to that of the diffused heat 50, reaching the air layer 16 in the crack defect 10 from the right. Heat diffusion in the object does not become discontinuous, since the amount of heat diffused from the left is equal to that of heat diffused from the right even if the crack defect 10 in the object 6 shuts off heat diffusion. Thus the crack defect 10 is difficult to detect, because the imaging signal from the crack defect does not markedly change.

The sixth embodiment differs from conventional infrared ray thermography in that, in the embodiment, the surroundings of an area to be imaged, not the whole object 6, are gradually heated to quickly detect a portion of the object which is nonhomogeneous in terms of thermal conductivity. Thus the present invention enables an object of high thermal conductivity, which is difficult to check for defects by conventional methods, to be inspected for defects by a highly sensitive method.

According to the sixth embodiment, changes in the intensity of the diffusion emission infrared rays 48, diffused from the limited heated area 46 to the imaging area 11 and emitted from the surface of the object 6, due to a crack defect in the imaging area 11 or thereabouts are used to detect the defect by emphasizing a signal part corresponding to it. Thus a crack detect can be detected which has an opening smaller than the value of the resolving power of the imaging means. This provides an inexpensive defect detecting apparatus that can fast detect a surface crack defect or an internal crack defect of the object 6 with high accuracy no matter whether the object diffuses light or not.

Referring to the embodiments, the present invention has been described in detail above. The embodiments described herein apply to detecting a crack defect of a ceramic substrate. The present invention, however, can apply to defects other than cracks, since the present invention is based on the principle that either light entering the object 6, gathering information on an optically nonhomogeneous portion of the object, and emitted from a surface thereof or light conducting heat through the object 6, gathering information on a portion of the object which is nonhomogeneous in terms of thermal conductivity, and emitted from a surface of the object is sensed to detect the optically nonhomogeneous portion or the portion which is nonhomogeneous in terms of thermal conductivity.

For example, the present invention enables an interface having a locally high index of reflectance or one having a locally low thermal conductivity to be detected.

We claim:

1. An optical defect detecting apparatus comprising:
    illuminating means for illuminating an inspected object so that light beams aimed at the object form a dotted line on a surface thereof,
    imaging means for detecting light beams emitted from a linear area parallel to an illuminated area formed on the surface of the object by said illuminating means,
    image processing means for detecting an optically unhomogeneous portion of said object based on an imaging signal detected by said imaging means, and
    drive means for relatively moving said object with respect to said illuminating means and said imaging means.

2. An optical defect detecting apparatus comprising:
    illuminating means for illuminating an inspected object by one-dimensionally scanning the object, while varying illumination intensity, imaging means for detecting light beams emitted from a linear area parallel to an illuminated area formed on the surface of the object by said illuminating means, image processing means for detecting an optically unhomogeneous portion of said object based on an imaging signal detected by said imaging means, and drive means for relatively moving said object with respect to said illuminating means and said imaging means.

3. An optical defect detecting apparatus comprising:

illuminating means for illuminating an inspected object by projecting light beams through slits forming a dotted line, imaging means for detecting light beams emitted from a linear area parallel to an illuminated area formed on the surface of the object by said illuminating means, image processing means for detecting an optically unhomogeneous portion of said object based on an imaging signal detected by said imaging means, and drive means for relatively moving said object with respect to said illuminating means and said imaging means.

4. An optical defect detecting apparatus comprising:

illuminating means for illuminating an inspected object through a reflector so that light beams aimed at the object form a dotted line on a surface thereof, imaging means for detecting through said reflector light beams emitted from a linear area parallel to an illuminated area formed on the surface of the object by said illuminating means, image processing means for detecting an optically unhomogeneous portion of said object based on an imaging signal detected by said imaging means, and drive means for turning said reflector back and forth by a predetermined angle.

5. An optical defect detecting apparatus comprising:

illuminating means for aiming light beams composed of light rays belonging to different wavelength bands at a surface of an inspected object so that the light beams differ in intensity at the surface and do not interfere with each other, chromatic resolving means for separating into wavelength bands light rays emitted from a parallel to an illuminated area formed on the surface of the object by said illuminating means to detect the rays, image processing means for detecting an optically unhomogeneous portion of said object based on an imaging signal detected by said imaging means, and drive means for relatively moving said object with respect to said illuminating means and said imaging means.

6. An optical method of detecting a defect, comprising the steps of:

(a) aiming light beams at a surface of an inspected object, said light beams differing in intensity in the form of a dotted line on the surface of the object;

(b) detecting light beams emitted from a linear area on the surface of the object after the light beams aimed at the surface of the object have entered the object; and (c) detecting an optically unhomogeneous portion of the object by detecting changes in the intensity of the light beams detected.

7. An optical method for detecting a defect, comprising the steps of:

(a) aiming light beams composed of light rays belonging to a plurality of wavelength bands at a surface of an inspected object, said light beams differing in intensity in the form of a dotted line on the surface of the object without interfering with each other;

(b) detecting light beams emitted from a linear area on the surface of the object after the light beams aimed at the surface of the object have entered the object; and (c) detecting an optically unhomogeneous portion of the object by detecting changes in the intensity of the light beams detected.

* * * * *